(12) United States Patent
Carter

(10) Patent No.: US 6,603,995 B1
(45) Date of Patent: Aug. 5, 2003

(54) BODY MONITORING APPARATUS

(75) Inventor: Hugh Carter, Edinburgh (GB)

(73) Assignee: Reynolds Medical Limited (GB)

( * ) Notice: Subject to any disclaimer, the term of this patent is extended or adjusted under 35 U.S.C. 154(b) by 226 days.

(21) Appl. No.: 09/692,962

(22) Filed: Oct. 19, 2000

(51) Int. Cl.$^7$ ................................................. A61B 5/04
(52) U.S. Cl. ........................................ 600/509; 607/17
(58) Field of Search ........................ 600/509, 510–520, 600/300, 549, 527; 128/903, 904, 901; 607/17–20

(56) References Cited

U.S. PATENT DOCUMENTS

| | | | | |
|---|---|---|---|---|
| 4,108,166 A | | 8/1978 | Schmid ................ 128/2.06 F |
| 4,459,992 A | * | 7/1984 | Gwyn ........................ 128/687 |
| 5,123,419 A | * | 6/1992 | Platt et al. .................. 128/697 |
| 6,238,354 B1 | * | 5/2001 | Alvarez ..................... 600/549 |
| 6,374,138 B1 | * | 4/2002 | Owen et al. .................... 607/2 |

\* cited by examiner

Primary Examiner—Mark Paschall
(74) Attorney, Agent, or Firm—Blakely, Sokoloff, Taylor & Zafman

(57) ABSTRACT

Portable ECG monitoring apparatus comprises a sensor device 1 detachable from a monitoring device 2. The sensor device includes ECG sensors attached via cabling 5 to a connector 4. The sensor device 1 and monitoring device 2 are connected by attaching the connector 4 to the monitoring device 2, which provides a watertight seal for the apparatus and prevents access to any internal components in the monitoring device 2.

12 Claims, 2 Drawing Sheets

BODY MONITORING APPARATUS

Figure 1:
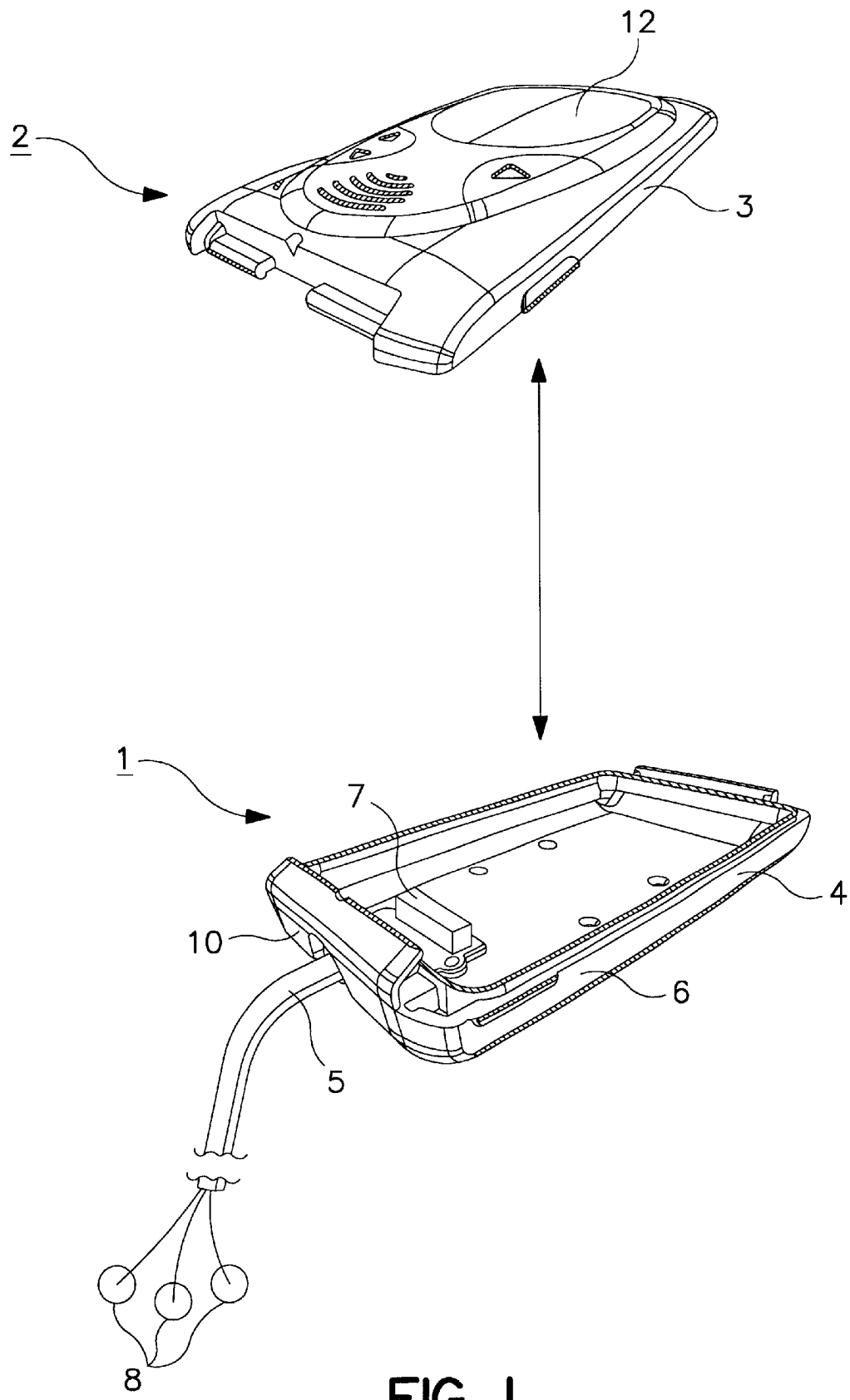

This invention relates to body monitoring apparatus, such as, for example, ECG monitoring apparatus.

Body monitoring apparatus generally includes physiological sensors, a monitoring device and cables connecting the sensors to the monitoring device. The sensors are attached to a patient's body to detect physiological signals and may be, for example, electrocardiogram (ECG) electrodes, electroencephalogram (EEG) electrodes or blood oxygen sensors. For example, in ECG monitoring apparatus an electrocardiogram signal is measured as the difference in potential between a set of electrodes placed externally on the body of the patient. This allows the cardiac activity to be measured.

In ambulatory monitoring the complete electronic apparatus is miniaturised and battery operated, adapted for wearing on the patient's body. WO94/26164 describes one known ambulatory monitoring apparatus, and is incorporated herein by reference.

In all types of body monitoring apparatus it is advantageous for safety reasons that the patient is electrically isolated from the apparatus in use. In particular that access to the power source and other electrical connections in the monitoring device are prevented.

According to the invention, there is provided body monitoring apparatus including a sensor device for detecting physiological signals and a monitoring device, the monitoring device including a first part of a casing and an electronics module, the sensor device including a second part of a casing, wherein a completed casing which surrounds the electronics module is provided by the first and second parts attached together when the sensor device is connected to the monitoring device.

Of the completed casing the first and second parts are the only detachable parts. These parts are designed to be detached by only authorised personnel and not the user. The user will regard the device as one sealed unit.

Preferably, the sensor device includes means for sensing potentials at points on the patient's body. In the embodiment the sensing means is permanently attached or incorporated into the sensor device. It is not possible to change the sensing means without detaching the sensor device from the monitoring device, i.e. splitting the completed casing apart.

Advantageously, the completed casing is watertight. Therefore the device can continue to operate even when exposed to moisture. Because the casing has only two parts, only one watertight seal is required.

The electronics module of the monitoring device in the embodiment includes a power source which can only be removed when the sensor device is not connected to the monitoring device. Detaching the sensor device from the monitoring device in the embodiment automatically shuts down the electronics. Therefore, the device cannot be damaged by removing the power source while the electronics are fully operational. Also, because the power source is inaccessible to the patient, a high power power source can be included in the apparatus.

The present invention also relates to a cabling device, a sensor device and a monitoring device all for use in the body monitoring apparatus as defined above.

Figure 2:
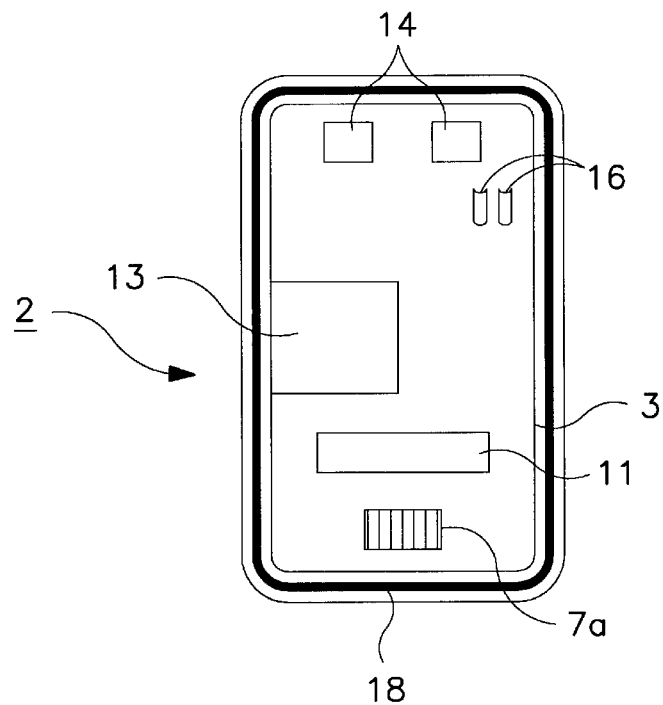
Figure 3:
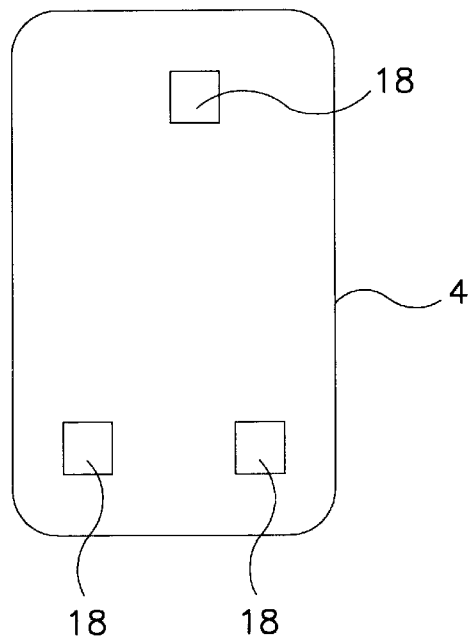

For a better understanding of the present invention, specific embodiments according to the invention will now be described by way of example, with reference to the accompanying drawings, in which FIG. 1 shows body monitoring apparatus according to the invention, FIG. 2 shows the underside of the monitoring device part of the apparatus, and FIG. 3 shows a modified sensor device part of the apparatus, in which electrodes are incorporated.

In FIG. 1, portable body monitoring apparatus is provided by a sensor device 1 and a monitoring device 2. The monitoring device 2 includes a first part 3 of a casing, and an electronics module 11 (FIG. 2). The sensor device 1 includes sensors 8 which may be, for example, ECG electrodes for attaching to the patient's body. The sensor device includes a cable 5 linking the sensors 8 to a connector 4. The connector 4 includes a second part 6 of the casing.

In use, the sensor device 1 is electrically connected to the monitoring device 2 by an electrical interconnect 7 in the connector 4 and a corresponding interconnect 7a in the monitoring device. The monitoring device 2 can then receive physiological data from the sensors 8 via the connector 4 and the cable 5.

Physiological data is received by the electronics module 11 in the monitoring device 2 and (depending on the particular electronics provided) may be displayed upon a front display panel 12 and/or transmitted to a remote station and/or stored in a memory device 13 for future display or transfer to other equipment (such as, for example, a personal computer). The monitoring device 2 may respond to the physiological data directly to produce an alarm or other indication to the patient or medical staff. The memory device 13 may be any suitable storage medium such as a magnetic cassette or solid state memory card.

The monitoring device 2 also includes batteries 14 and control switches 16 for configuring the monitoring device.

In the embodiment, the first part 3 of the casing is substantially planar and has a single opening in the back which extends substantially over the whole plan area of the casing. When the connector 4 is not connected to the monitoring device 2, the electronics in the monitoring device 2 are exposed and can be accessed through the opening. The medical staff are therefore able to replace the batteries 14 in the device, set control switches 16, and remove and replace the storage medium.

The second part 6 of the casing is provided by the external structure of the connector 4, which is a rigid moulding. When the connector 4 is connected to the back of the monitoring device 2 the first 3 and second 6 parts of the casing are attached together and the casing is thus completed. At the same time, electrical connection is provided between the sensors 8 and the monitoring device 2.

The entry of the cable 5 to the connector 4 is sealed by an elastomeric strain relief grommet 10. The grommet 10 is permanently fixed in place. The rigid moulding and elastomeric grommet assembly for the connector 4 is cheaper than alternative connector designs in which the electrical assembly is overmoulded with elastomers.

Connector mis-mating is prevented by the physical design of the connector 4. The connector can only be attached in one orientation.

When the casing is completed, no access is possible to the internal components 7a, 11, 13, 14 and 16 of the monitoring device 2. Therefore when the device 2 is in use on a patient, the patient is substantially electrically isolated from the device. It is not possible to access any of the electrical connections within the device (for example battery 14 terminals, memory card connections, conductive chassis) which could otherwise present a risk to the patient's safety. This allows additional battery capacity to be provided in the apparatus without increasing the risk to the patient's safety.

A watertight seal is provided between the first 3 and second 6 parts of the completed casing. This is provided by a foamed silicon rubber 'O' ring 18 located in a continuous channel running around the periphery of the opening in the first part 3 of the casing. A raised edge 9 of the second part 6 of the casing presses against this gasket ('O' ring) to form a seal. The completed casing is waterproof, and therefore advantageously resistant to fluid ingress, both in the patient environment (perspiration, ablutions, incontinence, rain) and in the medical environment (cleaning and disinfecting).

Thus a fluid-tight casing formed of two readily detachable parts is provided.

It is generally recognised as more difficult to provide seals for covers that are readily detachable from a body than to provide permanent fixed seals. In the embodiment the single connector 4 provides a simple and effective method for sealing the casing using a minimum number of opening seals.

Different types of physiological sensors and cables are available. The body monitoring apparatus of the embodiment incorporates circuitry which allows the monitoring device 2 to determine firstly if a sensor device 1 has been connected, and if so, what type of cable or sensor is being used. This "autosensing feature" is implemented using a coded interconnection of connector pins provided in the interconnect 7. This simplifies the set up procedure when changing sensors by minimising the required user interaction. In this way, the apparatus can detect whether a connector has been attached and therefore whether the casing is complete or incomplete. If a connector 4 is not attached, the monitoring device can enter a "safe mode" to prevent corruption of any recorded or internal data and/or to conserve battery life.

Additional circuitry which is specific to the physiological sensor type may be built as part of the connector 4. For example, a twelve lead ECG electrode connections, defibrillator protection and signal acquisition circuitry could be integrated as a patient cable.

The large area of the connector 4 allows the sensor device 1 to alternatively be manufactured as a direct electrode accessory, as shown in FIG. 3. In this, the connector 4 includes well separated conductive areas 18 which act as the electrodes when in contact with the patient. This arrangement is applicable to an ECG event recorder for example.

As an alternative to the sensors, the connector 4 can instead be provided with cabling for connecting the monitoring device 2 to other external equipment (for example, a personal computer). The connector can then be attached to the monitoring device 2 to provide a serial data communications link for downloading data stored in the storage medium to the external equipment. This maybe downloaded using a format such as RS-232 or USB. With this design, it is not possible for both the sensors and the external equipment to be simultaneously connected to the monitoring device and therefore avoids this potentially hazardous situation.

What is claimed is:

1. Body monitoring apparatus including a sensor device for detecting physiological signals and a monitoring device, the monitoring apparatus comprising a casing having a first and a second part, the monitoring device comprising an electronics module, the first part of the casing shaped so as to allow access to the electronics module, the sensor device including the second part of the casing wherein a completed casing which surrounds the electronics module is provided by the first and second parts attached together when the sensor device is connected to the monitoring device and wherein the casing is adapted such that access to the electronics module is prevented while the sensor device is connected to the monitor device.

2. Body monitoring apparatus according to claim 1, wherein the completed casing is watertight.

3. Body monitoring apparatus according to claim 2, wherein a watertight seal between the first and second parts of the completed casing is formed between an 'O' ring in a channel formed on one of first and second parts of the casing and a raised edge formed on the other part.

4. Body monitoring apparatus according to claim 1, the electronics module including a power source which can be removed when the sensor device is not connected to the monitoring device.

5. Body monitoring apparatus according to claim 1, the electronics module including a storage medium which can be removed when the sensor device is not connected to the monitoring device.

6. Body monitoring apparatus according to claim 1, the electronics module including an internal control switch which can be accessed when the sensor device is not connected to the monitoring device.

7. Body monitoring apparatus according to claim 1, including circuitry for detecting whether the casing is complete or incomplete.

8. Body monitoring apparatus according to claim 7, the circuitry including connector pins.

9. Body monitoring apparatus according to claim 1, wherein the sensor device includes means to sensing potentials at points on a living body.

10. A body monitoring apparatus comprising:
a sensor device for detecting physiological signals, the sensor device having a first casing;
a monitoring device including an electronics module, the monitoring device having a second casing that is removeably coupled to the first casing; and
a cabling device coupled to the sensor device,
wherein the second casing is shaped to allow access to the electronics module,
wherein the first casing and the second casing form a complete casing that surrounds the electronics module when the sensor device is connected to the monitoring device,
wherein the complete casing is adapted to prevent access to the electronics module while the sensor module is connected to the monitoring device, and
wherein the sensor device includes means for sensing potentials at points on a living body.

11. An apparatus comprising:
a sensor device for detecting physiological signals; and
a first casing coupled to the sensor device,
wherein the first casing is configured to couple to a second casing to form a complete casing that surrounds an electronics module of a monitoring device when the sensor device is connected to the monitoring device, and
wherein the complete casing is adapted to prevent access to the electronics module while the sensor module is connected to the monitoring device.

12. An apparatus comprising:
a first casing;
a monitoring device coupled to the first casing; and
an electronics module coupled to the monitoring device,
wherein the first casing is configured to couple to a second casing to form a complete casing that surrounds the electronics module when a sensor device is connected to the monitoring device, and
wherein the complete casing is adapted to prevent access to the electronics module while the sensor module is connected to the monitoring device.

* * * * *